United States Patent [19]

Miller

[11] Patent Number: 5,602,138

[45] Date of Patent: Feb. 11, 1997

[54] NKA AFFECTING PIPERIDYL HETEROBICYCLIC COMPOUNDS

[75] Inventor: Scott C. Miller, Newark, Del.

[73] Assignee: Zeneca Limited, London, United Kingdom

[21] Appl. No.: 349,117

[22] Filed: Dec. 2, 1994

[30] Foreign Application Priority Data

Dec. 7, 1993 [EP] European Pat. Off. .............. 9325074

[51] Int. Cl.⁶ ..................... C07D 239/80; C07D 401/14; A61K 31/445; A61K 31/505

[52] U.S. Cl. .......................... 514/259; 514/316; 514/322; 514/323; 544/284; 544/286; 546/187; 546/199; 546/201

[58] Field of Search ..................... 544/286, 284; 548/306.1, 466; 514/259, 387, 414, 316, 322, 323

[56] References Cited

U.S. PATENT DOCUMENTS 5,236,921  8/1993  Emonds-Alt et al. .................. 514/252

FOREIGN PATENT DOCUMENTS

| | | |
|---|---|---|
| 2029275 | 5/1991 | Canada . |
| 2067924 | 11/1992 | Canada . |
| 2090785 | 9/1993 | Canada . |
| 0428434 | 5/1991 | European Pat. Off. . |
| 0474561 | 3/1992 | European Pat. Off. . |
| 0512902 | 11/1992 | European Pat. Off. . |
| 0515240 | 11/1992 | European Pat. Off. . |
| 0512901 | 11/1992 | European Pat. Off. . |
| 0559538 | 9/1993 | European Pat. Off. . |
| 0625509 | 11/1994 | European Pat. Off. . |
| 0630887 | 12/1994 | European Pat. Off. . |
| 023178 | 1/1993 | South Africa . |
| 923177 | 1/1993 | South Africa . |
| WO94/10146 | 5/1994 | WIPO . |

OTHER PUBLICATIONS

A. Graham et al., "Isolation and Characterisation of the Human Lung NK–2 Receptor Gene Using Rapid Amplification of cDNA Ends", *Biochemical and Biophysical Research Communications*, (1991), vol. 177, No. 1, 8–16.

X. Emonds–Alt et al., "Pharmacological Profile and Chemical Synthesis of SR 48968, a Non–Peptide Antagonist of the Neurokinin A ($NK_2$) Receptor", *Biorganic & Medicinal Chemistry Letters*, (1993), vol. 3, No. 5, 925–930.

D. Aharony et al., "Pharmacologic Characterization of the Novel Ligand [4,5—³HH–LEU⁹]Neurokinin–A Binding to NK–2 Receptors on Hamster Urinary Bladder Membranes", (1992), 23, 121–130.

M. Needham et al., "LCR/MEL: A Versatile System for High–Level Expression of Heterologous Proteins in Erythroid Cells", *Nucleic Acids Research*, (1992), vol. 20, No. 5, 997–1003.

Primary Examiner—Matthew V. Grumbling
Attorney, Agent, or Firm—Robert J. Harris

[57] ABSTRACT

Compounds of formula I

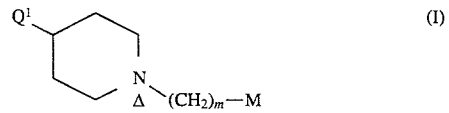

wherein $Q^1$, m and M have any of the meanings given in the specification, their N-oxides, and their pharmaceutically acceptable salts are nonpeptide antagonists of neurokinin A and useful for the treatment of asthma, etc. Also disclosed are pharmaceutical compositions, processes for preparing the compounds of formula I and intermediates.

8 Claims, No Drawings

NKA AFFECTING PIPERIDYL HETEROBICYCLIC COMPOUNDS

This invention concerns novel bicyclic heterocycles, and, more particularly, novel ortho-fused bicyclic heterocycles, which antagonize the pharmacological actions of one of the endogenous neuropeptide tachykinins known as neurokinins, particularly at the neurokinin 2 (NK2) receptor. The novel bicyclic heterocycles are useful whenever such antagonism is desired. Thus, such compounds may be of value in the treatment of those diseases in which an NK2 receptor is implicated, for example, in the treatment of asthma and related conditions. The invention also provides pharmaceutical compositions containing the novel bicyclic heterocycles for use in such treatment, methods for their use, and processes and intermediates for the manufacture of the novel bicyclic heterocycles.

The mammalian neurokinins comprise a class of peptide neurotransmitters which are found in the peripheral and central nervous systems. The three principal neurokinins are Substance P (SP), Neurokinin A (NKA) and Neurokinin B (NKB). There are also N-terminally extended forms of at least NKA. At least three receptor types are known for the three principal neurokinins. Based upon their relative selectivities favoring the neurokinin agonists SP, NKA and NKB, respectively, the receptors are classified as neurokinin 1 (NK1), neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation and activation of mast cells. Thus, the tachykinins are implicated in the pathophysiology and the airway hyperresponsiveness observed in asthmatics; and blockade of the action of released tachykinins may be useful in the treatment of asthma and related conditions. Peptidic NK2 antagonists have been reported. For example, a cyclic hexapeptide known as L-659,877 has been reported as a selective NK2 antagonist. Nonpeptidic NK2 antagonists also have been reported, for example in European Patent Application, Publication Number (EPA) 428434, EPA 474561 EPA 512901, EPA 512902 and EPA 515240, as well as in EPA 559538. I have discovered a series of nonpeptidic NK2 antagonists, and this is the basis for my invention.

According to the invention, there is provided a Compound of the invention which is a compound of formula I (formula set out hereinbelow following the Examples, together with other formulae denoted by Roman numerals) wherein $Q^1$ is a nitrogen linked radical of formula II wherein $E^1$, $E^2$, $E^3$ and $E^4$ form a divalent four membered chain ($-E^1=E^2-E^3=E^4-$) in which each of $E^1$, $E^2$, $E^3$ and $E^4$ is methine; or in which one of $E^1$, $E^2$, $E^3$ and $E^4$ is nitrogen and the remaining three are methine; wherein the radicals F, G, and I(X) are selected from:

(i) G is a direct bond, I(X) is a radical having the formula $=C(Z)-$ and F is a radical selected from $-CH=$ and $-N=$;

(ii) G is a direct bond, I(X) is a radical having the formula $-C(=J)-$ and F is a radical selected from $-N(R^f)-$, $-CH_2-CH_2-$, $-CH=CH-$, $-CH_2-N(R^f)-$ and $-CH=N-$;

(iii) G is a radical having the formula $-CH_2-$, I(X) is a radical having formula $-C(=J)-$ and F is selected from $-CH_2-$ and $-N(R^f)-$; and (iv) G is selected from $-CH_2-$, $-CH_2-CH_2-$, $-CH=CH-$ and $-N=CH-$, I(X) is a radical having the formula $-C(=J)-$ and F is a direct bond;

J is oxygen or, sulfur;

Z is $-OR^a$, $-SR^a$, $-C(=O)R^a$, $-C(=O)OR^a$, $-C(=J^a)NR^bR^c$ or $-C(R^a)(OR^d)(OR^e)$;

$J^a$ is oxygen or sulfur;

$R^a$ and $R^f$ are independently hydrogen or (1–6C)alkyl;

$R^b$ and $R^c$ are independently hydrogen or (1–6C)alkyl; or $R^b$ and $R^c$ together with the nitrogen to which they are attached form a pyrrolidino, piperidino, morpholino, thiomorpholino (or its S-oxide) or piperazinyl group (which piperazinyl group may bear a methyl or ethyl group at the 4-position);

$R^d$ and $R^e$ are independently (1–3C)alkyl or $R^d$ and $R^e$ together form ethylene or trimethylene;

m is 2 or 3;

M is a residue of formula Ia or formula Ib wherein

Q is phenyl which may bear one or two substituents independently selected from halo, trifluoromethyl, hydroxy, (1–3C)alkoxy, (1–3C)alkyl and methylenedioxy; or Q is thienyl, imidazolyl, benzo[b]thiophenyl or naphthyl any of which may bear a halo substituent; or Q is biphenylyl; or Q is carbon-linked indolyl which may bear a benzyl substituent at the 1-position;

$Q^a$ is hydrogen, (1–4C)alkyl, or a radical of formula $-(CH_2)_q-NR^7R^8$ in which q is 2 or 3 and $R^7$ and $R^8$ are independently (1–4C)alkyl or $NR^7R^8$ is piperidino or 4-benzylpiperidino;

$R^3$ is hydrogen, methyl or (2–6C)n-alkyl which may bear a terminal amino radical;

$R^4$ is $-C(=O)R^5$, $-C(=O)OR^5$ or $-C(=J^1)NHR^5$ in which $J^1$ is oxygen or sulfur and $R^5$ is hydrogen, (1–6C)alkyl, phenyl(1–3C)alkyl (in which the phenyl may bear one or more halo, hydroxy, (1–4C)alkoxy or (1–4C)alkyl substituents), pyridyl(1–3C)alkyl, naphthyl(1–3C)alkyl, pyridylthio(1–3C)alkyl, styryl, 1-methylimidazol-2-ylthio(1–3C)alkyl, aryl (which may bear one or more halo, hydroxy, (1–4C)alkoxy or (1–4C)alkyl substituents), heteroaryl (which may bear one or more halo, hydroxy, (1–4C)alkoxy or (1–4C)alkyl substituents), or (when $R^4$ is $-COR^5$) α-hydroxybenzyl;

n is 0, 1, 2 or 3;

p is 1 or 2, and when p is 2, n is 1 and $J^2$ is two hydrogens;

$J^2$ is oxygen or two hydrogens;

$L^1$ is carbonyl or methylene;

r is 0, 1, 2, or 3; and $R^6$ is phenyl which may bear one or more halo, trifluoromethyl, (1–4C)alkyl, hydroxy or (1–4C)alkoxy substituents (and particularly one or, more chloro or fluoro substituents); naphthyl which may bear one or more halo, trifluoromethyl, (1–4C)alkyl or hydroxy substituents; pyridyl; thienyl; indolyl; quinolinyl; benzothienyl or imidazolyl; or when $L^1$ is carbonyl, the group $-(CH_2)_r-R^6$ may represent aryl, heteroaryl or a benzyl group bearing an α-substituent selected from hydroxy, (1–4C)alkoxy and (1–4)alkyl, and further wherein the aryl, heteroaryl or phenyl portion of the benzyl group may bear one or more substituents selected independently from halo, trifluoromethyl, (1–4C)alkyl, hydroxy and (1–4C)alkyl, hydroxy and (1–4C)alkoxy (and particularly one or more chloro or fluoro substituents);

or the N-oxide of the piperidino nitrogen indicated by Δ;

or a pharmaceutically acceptable salt thereof;

or a quaternary ammonium salt thereof, —0= in which the piperidino nitrogen indicated by Δ is a quadricovalent ammonium nitrogen wherein the fourth radical on the nitrogen $R^9$ is (1–4C)alkyl or benzyl and the associated counterion A is a pharmaceutically acceptable anion.

A subgroup of the invention is a compound of formula Ic; or the N-oxide of the piperidinio nitrogen indicated by Δ; or a pharmaceutically acceptable salt thereof; or a quaternary ammonium salt thereof; wherein $Q^1$ has any of the values defined above for a compound of formula I.

It will be appreciated that a compound of formula I (or Ic) contains one or more asymmetrically substituted carbon atoms such that such a compound may be isolated in optically active, racemic and/or diastereomeric forms. It will further be appreciated that a compound of formula I (or Ic) may exist in tautomeric forms and that a compound may exhibit polymorphism. It is to be understood that the present invention encompasses any racemic, optically-active, diastereomeric, tautomeric, polymorphic or stereoisomeric form, or mixture thereof, which form possesses NK2 antagonist properties, it being well known in the art how to prepare optically-active forms (for example, by resolution of the racemic form or by synthesis from optically-active starting materials) and how to determine the NK2 antagonist properties by the standard tests described hereinafter. It may be preferred to use the compound of formula I (or Ic) in a form which is characterized as containing, for example, at least 95%, 98% or 99% enantiomeric excess. Further, it may be preferred to use the compound of formula Ic in a form which is characterized as containing, for example, at least 95%, 98% or 99% enantiomeric excess of the form with the (S)-configuration at the center indicated by * in the formula.

In this specification $R^a$, $R^b$, $R^1$, $R^2$, et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five ring atoms consisting of carbon and one to four heteroatoms selected from oxygen, sulfur and nitrogen or containing six ring atoms consisting of carbon and one or two nitrogens, as well as a radical of an ortho-fused bicyclic heterocycle of about eight to ten atoms derived therefrom, particularly a benz-derivative or one derived by fusing a propenylene, trimethylene of tetramethylene diradical thereto, as well as a stable N-oxide thereof.

A pharmaceutically acceptable salt is one made with an acid which provides a physiologically acceptable anion.

Particular values are listed below for radicals, substituents and ranges for a compound of formula I or formula Ic as described above for illustration only and they do not exclude other defined values or other Values within defined ranges for the radicals and substituents.

A particular value for m is 2.

A particular value for (1–6C)alkyl is methyl, ethyl, propyl, isopropyl or butyl.

A particular value for (1–3C)alkyl is methyl or ethyl.

When M is formula Ia, a particular value for $Q^a$ is hydrogen, a particular value for $R^3$ is methyl and a particular value for $R^4$ is —$COR^5$. A particular value for $R^5$ is aryl, and more particularly phenyl, which aryl (or phenyl) may bear one or two chloro or fluoro substituents.

When M is formula Ib, a particular value for n is 1 or 2; a particular value for p is 1; a particular value for $J^2$ is two hydrogens; a particular value for $L^1$ is carbonyl; a particular value for r is 0 or 1; and a particular value for $R^6$ is phenyl which may bear one or two halo or (1–4C)alkoxy substituents, and more particularly a chloro, fluoro or isopropoxy substituent.

A particular value for Q is, for example, phenyl which may bear one or two substituents selected from halo, trifluoromethyl and methylenedioxy; and, more particularly, 3,4-dichlorophenyl or 3,4-methylenedioxyphenyl.

A particular value for $R^9$ is methyl or benzyl and for A is, for example, chloride, bromide or methanesulfonate.

A particular subgroup of the invention is a compound of formula Ic wherein each of $E^1$, $E^2$, $E^3$ and $E^4$ is methine Another particular subgroup of the invention is a compound of formula Ic wherein one of $E^1$, $E^2$, $E^3$ and $E^4$ is nitrogen and the remaining three are methine.

Another particular subgroup of the invention is a compound of formula I or Ic wherein each of $E^1$, $E^2$, $E^3$ and $E^4$ is methine G is a direct bond, I(X) is a radical having the formula —C(=J)— and F is a radical selected from —$CH_2$—$CH_2$—, —CH=CH—, and —CH=N—.

Another particular subgroup of the invention is a compound of formula I or Ic wherein one of $E^1$, $E^2$, $E^3$ and $E^4$ is nitrogen and the remaining three are methine, G is a direct bond, I(X) is a radical having the formula —C(=J)— and F is —$CH_2$—$CH_2$—, and more particularly wherein $E^4$ is nitrogen.

A particular value for $Q^1$ is a nitrogen linked radical selected from the radicals set out in formulae VII, VIII, IX, XIV, XV, XVI, XVII, XVIII, XIX, XX, XXI, and XXII.

Another particular value for $Q^1$ is a nitrogen linked radical selected from the radicals set out in formulae X and XI.

A more particular value for $Q^1$ is a nitrogen linked radical selected from the radicals set out in formulae VII, VIII and IX.

Pharmaceutically acceptable salts of a compound of formula I (or of formula Ic) include those made with a strong inorganic or organic acid which affords a physiologically acceptable anion, such as, for example, hydrochloric, sulfuric, phosphoric, methanesulfonic, or para-toluenesulfonic acid.

A compound of formula I (or of formula Ic) may be made by processes which include processes known in the chemical art for the production of structurally analogous heterocyclic compounds. Such processes and intermediates for the manufacture of a compound of formula I (or of formula Ic) as defined above are provided as further features of the invention and are illustrated by the following procedures in which the meanings of generic radicals are as defined above unless otherwise indicated:

(a) Alkylating a piperidine of formula III with an aldehyde of formula IV (or of formula IVc), by reductive alkylation. The alkylation is preferably carried out by a conventional reductive alkylation, for example as described in Example 1, by the in situ, acid-catalyzed formation of an imminum salt, followed by reduction with sodium cyanoborohydride in alcoholic solvent.

(b) Alkylating a piperidine of formula III with an alkylating agent of formula V (or of formula Vc) in which Y is a leaving group. Typical values for Y include for example, iodide, bromide, methanesulfonate, p-toluenesulfonate, trifluoromethane-sulfonate, and the like.

(c) For an N-oxide of the piperidino nitrogen indicated by Δ a of a compound of formula I (or of formula Ic), oxidizing the piperidino nitrogen indicated by Δ of a compound of formula I using a conventional procedure, such as, for example, using hydrogen peroxide in methanol, peracetic acid, 3-chloroperoxybenzoic acid in an inert solvent (such as dichloromethane) or dioxirane in acetone.

(d) For a quaternary ammonium salt of a compound of formula I (or of formula Ic), alkylating the piperidino nitrogen indicated by Δ of the compound of formula I (or of formula Ic) with an alkylating agent of formula $R^9Y$, followed, if required, by exchanging the counterion Y for a different counterion A by a conventional method. Typical values for Y include those listed above under (a) for Y. Exchange of counterions may conveniently be carried out using a basic ion exchange resin in the "A" form.

(e) For a quaternary ammonium salt of a compound of formula I (or of formula Ic), alkylating a piperidine of formula IIIa with an alkylating agent of formula V, in which Y is a leaving group, followed, if required, by exchanging the counterion Y for a different counterion A by a conventional method. Typical values for Y include those listed above under (a) for Y. Exchange of counterions may conveniently be carried out using a basic ion exchange resin in the "A" form.

It may be desired to optionally use a protecting group during all or portions of the above described processes; the protecting group then may be removed when the final compound is to be formed.

Whereafter, for any of the above procedures, when a pharmaceutically acceptable salt of a compound of formula I is required, it may be obtained by reacting the compound of formula I with an acid affording a physiologically acceptable counterion or by any other conventional procedure.

It will also be appreciated that certain of the various optional substituents in the compounds of the invention may be introduced by standard aromatic substitution reactions or generated by conventional functional group modifications either prior to or immediately following the processes above, and as such are included in the process aspect of the invention. Such reactions and modifications include, for example, introduction of nitro or halogeno and reduction of nitro. The reagents and reaction conditions for such procedures are well known in the chemical art.

If not commercially available, the necessary starting materials for the above procedures may be made by procedures which are selected from standard techniques of heterocyclic chemistry, techniques which are analogous to the synthesis of known, structurally similar compounds (particularly those described in the above noted EPA publications and their counterparts), and techniques which are analogous to the above described procedures or the procedures described in the Examples. The starting materials and the procedures for their preparation are additional aspects of the invention.

A convenient intermediate for preparation of starting materials of formulae IV, and V (or formula IVc and Vc) is an alcohol of formula VI (or formula VIc). The preparation of an optically active alcohol of formula VIc is described in Example 1, parts a.–h.; An alcohol of formula VI (or formula VIc) may then be oxidized to the aldehyde of formula IV (or formula IVc), for example using oxalyl chloride, dimethyl sulfoxide and triethylamine or using Dess-Martin periodinane (1,1,1-triacetoxy-1,1-dihydro-1,2-benziodoxol-3(1H)-one) as described in Example 1.i.; or it may be converted into an alkylating agent of formula V (or formula Vc) by a conventional procedure.

An intermediate of formula III can be prepared from an intermediate of formula IIIb by removal of the group $R^p$, for example as described in Example 1, part p. for 4-(1-oxo-1, 3-dihydro-isoindol-2-yl)piperidine.

When a compound of formula III is required in which J or $J^a$ is sulfur, it conveniently may be obtained from a corresponding 1-protected piperidine intermediate of formula IIIb, wherein J is oxygen and $R^p$ is a conventional nitrogen protecting group, by treatment with phosphorous pentasulfide or with Lawesson's reagent, 2,4-bis(4-methoxyphenyl)-1,3-dithia-2,4-diphosphetane-2,4-disulfide, followed by deprotection of the piperidine nitrogen.

A starting material piperidine of formula IIIa may be obtained from a piperidine of formula III by alkylation or reductive alkylation to introduce the substutient $R^9$.

An intermediate of formula IIIb, wherein $R^p$ is a conventional nitrogen protecting group, such as for example benzyloxycarbonyl, can be prepared as described in Example 1, parts j.–o. for 1-benzyloxycarbonyl-4-(1-oxo-1,3-dihydroisoindol-2-yl)-piperidine, or as described in Example 3, parts a.–d. for 1-benzyloxy-carbonyl-4-(2-oxo-1,2,3,4-tetrahydroquin-azolin-3-yl)piperidine.

A variety of sequences for the preparation of an intermediate of formula IIIb, wherein $R^p$ is a conventional nitrogen protecting group, such as for example benzyl or benzyloxycarbonyl, are known in the chemical art. For example, an intermediate of formula IIIb wherein $Q^1$ is a radical of formula X, XIV, XV, or XVI, can be prepared from a compound of formula XIII, using procedures similar to those described in International Patent Application, International Publication Number WO 92/12153. An intermediate of formula IIIb wherein $Q^1$ is a radical of formula XVII can be prepared as described in U.S. Pat. No. 3,325,499. An intermediate of formula IIIb wherein $Q^1$ is a radical of formula XVIII can be prepared as described in U.S. Pat. No. 4,029,795. An intermediate of formula IIIb wherein $Q^1$ is a radical of formula XIX or XX can be prepared as described in: Hidenori, O. et al. "Orally Active, Nonpeptide Vasopressin V1 Antagonists. A Novel Series of 1-(1-Substituted 4-piperidyl)-3,4-dihydro-2(1H)-quinolinone" *J. Med. Chem*, 1993, 36, 2011–2017. An intermediate of formula IIIb wherein $Q^1$ is a radical of formula XXI can be prepared as described in: Takai, H., et al. "Synthesis of 1- and 3-(1-Substituted 4-Piperidinyl)-1,2,3,4-tetrahydro-2-oxoquinazolines as Potential Antihypertensive Agents" *Chem. Pharm. Bull.*, 1985, 33, 1116–1128. An intermediate of formula IIIb wherein $Q^1$ is a radical of formula XXII can be prepared as described in German Patent DE 2,731,299.

As will be clear to one skilled in the art, a variety of sequences are available for preparation of the starting materials, and the sequences leading to the starting materials and products of the invention may be altered if appropriate considerations regarding the synthetic methods and radicals present are followed.

The utility of a compound of the invention or a pharmaceutically acceptable salt thereof (hereinafter, collectively referred to as a "Compound") may be demonstrated by standard tests and clinical studies, including those disclosed in the EPA publications noted above, such as EPA 428434 or EPA 474561, and those described below.

Neurokinin A (NKA) Receptor-binding Assay (Test A)

The ability of a Compound of the invention to antagonize the binding of NKA at the NK2 receptor may be demonstrated using an assay using the human NK2 receptor expressed in Mouse Erythroleukemia (MEL) cells, as described in: Aharony, D., Little, J., Thomas, C., Powell, S., Berry, D. and Graham, A. Isolation and Pharmacological Characterization of a Hamster Neurokinin A Receptor cDNA, *Molecular Pharmacology*, 1994, 45, 9–19. In an initial use of this assay, the $IC_{50}$ measured for the standard compound L-659,877 was found to be 30 nM versus $^3$H-NKA binding to MEL.

The selectivity of a Compound for binding at the NK2 receptor may be shown by determining its binding at other receptors using standard assays, for example, one using a tritiated derivative of SP in a tissue preparation selective for NK1 receptors or one using a tritiated derivative of NKB in a tissue preparation selective for NK3 receptors.

Guinea Pig Assay (Test B)

The ability of a Compound of the invention to antagonize the action of an agonist, either NKA or [β-ala$^8$]-NKA(4–10), in a pulmonary tissue may be demonstrated using a functional assay in guinea pig trachea, which is carried out as follows. The chosen agonist is referred to as AG throughout the description.

Male guinea pigs are killed by a sharp blow to the back of the head. The trachea are removed, trimmed of excess tissue and divided into two segments. Each segment is suspended as a ring between stainless steel stirrups in water-jacketed (37.5° C.) tissue baths containing a physiological salt solution of the following composition (mM): NaCl, 119; KCl 4.6; $CaCl_2$, 1.8; $MgCl_2$, 0.5; $NaH_2PO_4$, 1; $NaHCO_3$, 25; glucose, 11; thiorphan, 0.001; and indomethacin, 0.005; gassed continuously with 95% $O_2$–%5 $CO_2$. Initial tension placed on each tissue is 1 g, which is maintained throughout a 0.5 to 1.5 hour equilibration period before addition of other drugs. Contractile responses are measured on a Grass polygraph via Grass FT-03 force transducers.

Tissues are challenged repetitively with a single concentration of AG (10 nM) with intervening 30 min periods with washing to allow the tension to return to baseline levels. The magnitude of the contractions to AG reaches a constant level after two challenges, and each Compound is tested for inhibition of responses to AG by addition to the tissue bath 15 minute before the third or subsequent exposure to the agonist. The contractile response to AG in the presence of Compound is compared to that obtained with the second AG challenge (in the absence of Compound). Percent inhibition is determined when a Compound produces a statistically significant (p<0.05) reduction of the contraction and is calculated using the second contractile response as 100%.

Potencies of selected Compounds are evaluated by calculating apparent dissociation constants ($K_B$) for each concentration tested using the standard equation:

$$K_B = [\text{antagonist}]/(\text{dose ratio}-1)$$

where dose ratio=antilog[(AG–log molar $EC_{50}$ without Compound)–(AG –log molar $EC_{50}$ with Compound)]. The $K_B$ values may be converted to the negative logarithms and expressed as –log molar $K_B$ (i.e. $pK_B$). For this evaluation, complete concentration-response curves for AG are obtained in the absence and presence of Compound (30 min incubation period) using paired tracheal rings. The potency of AG is determined at 50% of its own maximum response level in each curve. The $EC_{50}$ values are converted to the negative logarithms and expressed as –log molar $EC_{50}$. Maximum contractile responses to AG are determined by expressing the maximum response to AG as a percentage of the contraction caused by carbachol (30 μM), added after the initial equilibration period. When a statistically significant (p<0.05) reduction of the maximum response to AG is produced by a compound, the percent inhibition is calculated relative to the percentage of carbachol contraction in the untreated, paired tissue used as 100%.

Guinea Pig Labored Abdominal Breathing (Dyspnea) Assay (Test C)

Activity of a Compound of the invention as an antagonist of NKA at the NK2 receptor also may be demonstrated in vivo in laboratory animals, for example by adapting a routine guinea pig aerosol test described for evaluation of leukotriene antagonists by Snyder, et al. (Snyder, D. W., Liberati, N. J. and McCarthy, M. M. Conscious guinea-pig aerosol model for evaluation of peptide leukotriene antagonists. *J. Pharmacol. Meth.* (1988) 19, 219). Using the clear plastic chamber described previously by Snyder et al. to secure guinea pigs for a head-only aerosol exposure to bronchoconstrictor agonists, agonist is administered by aerosol to six conscious guinea pigs simultaneously during each maneuver. The tachykinin NK2-selective agonist, [β-ala$^8$]-NKA(4–10), $3\times10^{-5}$ M, is aerosolized from a Devilbiss Model 25 ultrasonic nebulizer into an air stream entering the chamber at a rate of 2 L/minute.

Guinea pigs (275–400 g) are fasted for approximately 16 hours prior to experimentation. Compounds to be evaluated for blockade of effects of [β-ala$^8$]-NKA(4–10) or their vehicle (10% PEG400 in saline) are administered p.o. or i.v. at various times before aerosol agonist challenge. All animals are pretreated with atropine (10 mg/kg, i.p., 45 minutes pretreatment) indomethacin (10 mg/kg, i.p., 30 minutes pretreatment), propranolol (5 mg/kg, i.p., 30 minutes pretreatment), and thiorphan (1 mg/ml aerosol for 5 minutes, 15 minutes pretreatment).

Aerosol challenge with the agonist produces an initial increase in respiratory rate followed by a decrease with early signs of minor involvement of the abdominal muscles. The respiratory rate decreases further and the breathing becomes more labored with greater involvement of the abdominal muscles as exposure continues. The distinctly recognizable end point is the point where the breathing pattern of the guinea pig is consistently slow, deep, and deliberate, showing marked involvement of the abdominal muscles. Time, in seconds, from the onset of aerosol challenge to this end point is determined for each animal by using a stopwatch. The animals generally collapse after teaching the end point and donor recover from the agonist-induced respiratory distress. Antagonists result in an increase in the time to reach the end point. Animals receive the aerosol administration of agonist for a maximum time of 780 seconds.

Differences between drug treated groups and corresponding vehicle treated control groups are compared using Student's t-test for unpaired observations.

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in Test A or Test B is not limited to asthma, but rather, that the test provides evidence of general antagonism of NKA. In general, the Compounds of the invention which were tested demonstrated statistically significant activity in Test A with a $K_i$ of 1 µM or much less. In Test B, a $pK_B$ of 5 or greater was typically measured for a Compound of the invention. It should be noted that there may not always be a direct correlation between the activities of Compounds measured as $K_i$ values in Test A and the values measured in other assays, such as the $pK_B$ measured in Test B.

As discussed above, a compound of formula I or a pharmaceutically acceptable salt thereof possesses NKA antagonist properties. Accordingly, it antagonizes at least one of the actions of NKA which are known to include bronchoconstriction, increased microvascular permeability, vasodilation and activation of mast cells. NKA antagonists have also been reported to be useful for the treatment of diseases including arthritis, inflamation pain, gastrointestinal-hypermotility, Huntington's Disease, psychoses, hypertension, migrane and uticaria (U.S. Pat. No. 5,236,921). Accordingly, one feature of the invention is the use of a compound of formula I or a pharmaceutically acceptable salt thereof in the treatment of a disease in a human or other mammal in need thereof in which NKA is implicated and antagonism of its action is desired, such as for example the treatment of asthma or a related disorder. In addition, another feature of the invention is provided by the use of a compound of formula I or a salt thereof as a pharmacological standard for the development and standardization of new disease models or assays for use in developing new therapeutic agents for treating the diseases in which NKA is implicated Or for assays for their diagnosis.

When used in the treatment of such a disease, a compound of the invention is generally administered as an appropriate pharmaceutical composition which comprises a compound of formula I or a pharmaceutically acceptable salt thereof as defined hereinbefore and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration; sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received. It will be understood that generally equivalent amounts of a pharmaceutically acceptable salt of a compound of formula I may be used.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous sodium sulfate; evaporation of solvent was carried out using a rotary evaporator under reduced pressure (600–4000 pascals; 4.5–30 mm with a bath temperature of up to 60° C.;

(iii) chromatography means 'flash chromatography' (method of Still) carried out on Merck Kieselgel (Art 9385 from E. Merck, Darmstadt, Germany); reversed phase silica gel means octadecylsilane (ODS) coated support having a particle diameter of 32–74µ, known as "PREP-40-ODS" (Art 731740-100 from Bodman Chemicals, Aston, Pa., U.S.A.); thin layer chomatography (TLC) was carried out on 0.25 mm silica gel GHLF plates (Art 21521 from Analtech, Newark, Del., U.S.A.);

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) final products had satisfactory nuclear magnetic resonance (NMR) spectra and were substantially pure by TLC;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using $CDCl_3$ as solvent; conventional abbreviations for signal shape are used; for AB spectra the directly observed shifts are reported; "DMSO-$d^6$" means perdeuterio dimethyl sulfoxide;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume: volume (v/v) terms; and (xii) mass spectra (MS) were run with an electron energy of 70 electron volts in the chemical ionization mode using a direct exposure probe; generally only peaks which indicate the parent mass are reported.

Example 1

(S)-N-[2-(3,4-Dichlorophenyl) -4- [4-(1-oxoisoindolin-2-yl) piperidino]butyl]-N-methylbenzamide hydrochloride (S)-N-[2-(3,4-Dichlorophenyl)-4-oxobutyl]-N-methylbenzamide (270 mg) in methanol (2 mL) was added to a solution of 4-(1-oxoiso-indolin-2-yl) piperidine (200 mg) and acetic acid (0.053 mL) in methanol (3 mL). After 15 minutes, sodium cyanoborohydride (58 mg) in methanol (1 mL) was added in a single portion. After 6 hours, the reaction mixture was diluted with aqueous sodium bicarbonate, stirred for 30 minutes, and extracted with dichloromethane. The organic extracts were dried, evaporated, and chromatographed, with dichloromethane:methanol(gradient 98:2, 95:5) as the eluent. The resulting material was dissolved in dichloromethane, precipitated out as the hydrochloride salt with ethereal hydrogen chloride, evaporated, and placed under high vacuum overnight to give the title compound (390 mg) as a white solid; MS: m/z=550(M+1). Analysis for $C_{31}H_{33}Cl_2N_3O_2 \cdot 1.65$ HCl·0.40 $(CH_3CH_2)_2O$: Calculated: C, 61.14; H, 6.08; N, 6.56; Found: C, 61.09; H, 6.10; N, 6.48.

The (S)-N-[2-(3,4-dichlorophenyl)-4-oxobutyl]-N-methylbenzamide was prepared as follows:

a. 1-Bromo-2-(tetrahydropyran-2-yloxy)ethane. To a mechanically stirred solution of dihydropyran (1 L) and a strong acid ion exchange resin (10.0 g) in hexane (2 L) was added 2-bromoethanol (985 g) dropwise over a period of 1.5 hours. Throughout the addition, a cold water bath was used to maintain an internal temperature of 35°–40° C. After being stirred overnight at room temperature, the reaction mixture was chromatographed, eluting with hexane (6 L). The eluent was evaporated to give an amber liquid which was distilled through a 2 inch vigreux column. The material boiling between 75°–95° C. (3,300–4,700 Pa) was collected and redistilled to give the ether (1195.5 g) as an oil; bp 80°–90° C. (2666 Pa); NMR: 4.68 (m,1), 4.01 (m,1), 3.89 (m,1), 3.77 (m,1), 3.52 (m,3), 1.75–1.50 (m,6).

b. 2-(3,4-Dichlorophenyl)-4-(tetrahydropyran-2-yloxy)-butyronitrile. To a solution of sodium hydride (218.0 g of a 55% oil suspension) in tetrahydrofuran (4 L) at 10° C. in an ice/water bath was added 3,4-dichlorophenylacetonitrile (893.0 g) in tetrahydrofuran (2 L) over a period of 45 minutes and the resulting solution was allowed to stir for 2 hours at room temperature. The mixture was cooled in an ice/water bath and 1-bromo-2-(tetrahydropyran-2-yloxy)ethane (1076.0 g) was dropped in as a neat oil over a period of 25 minutes. The mixture was stirred overnight at room temperature and divided into four 2-liter portions. Each portion was diluted with saturated ammonium chloride (3 L) and extracted with ether (500 mL). The combined organic layers were washed (aqueous ammonium chloride), dried, and evaporated. The resulting material was chromatographed, with hexane:dichloromethane (gradient 100:0, 0:100) as the eluent, to give the nitrile (932 g) as an oil; NMR: 7.47 (m, 4), 7.20 (m,2), 4.57 (m,2), 4.08 (m,2), 3.85 (m,4), 3.54 (m,3), 3.37 (m,1), 2.15 (m,4), 1.77 (m,4), 1.56 (m,8).

c. 2-(3,4-Dichlorophenyl)-4-(tetrahydropyran-2-yloxy)butyl-amine. To a solution of the above nitrile (128.3 g) in 95% ethanol (1.1 L) and concentrated ammonium hydroxide (550 mL) was added Raney Nickel (25.0 g). The mixture was placed under a hydrogen atmosphere (3.6 bar) for 1.5 days. The mixture was filtered through diatomaceous earth to remove the catalyst, and the resulting filtrate was evaporated. The resulting material was chromatographed, with dichloromethane:methanol (gradient 100:0, 95:5) as the eluent, to give the amine (91 g) as an oil; MS: m/z=318(M+1), 234[(M+1)-tetrahydropyranyl]; NMR: 7.40 (s,1), 7.38 (s,1), 7.32 (d, 1, J=2.1), 7.28 (d,1, J=2.0), 7.07 (dd,1, J=2.1, 4.9), 7.04 (dd,1, J=2.1, 4.9), 4.50 (m,1), 4.43 (m,1), 3.70 (m,4), 3.45 (m,2), 3.27 (m,1), 3.17 (m, 1), 2.97–2.75 (m,6), 2.00 (m2), 1.82–1.66 (m,6), 1.53 (m,8), 1.18 (broad s,4).

d. 2-(3,4-Dichlorophenyl)-4-hydroxybutylamine. To a mechanically stirred solution of 2-(3,4-dichlorophenyl)-4-(tetrahydropyran-2-yloxy) butylamine (550 g) in methanol (3.3 L ) was added in one portion 6.0 N hydrochloric acid (352 mL), resulting in a slight exotherm. After being stirred for 3 hours, the reaction mixture was evaporated, and the residue was diluted with water to 3 L volume. This solution was extracted with ether (2 times 500 mL), basified with sodium hydroxide pellets (100 g), and extracted with ethyl acetate (4 times 500 mL). The combined ethyl acetate extracts were washed (800 mL saturated sodium chloride), dried, and evaporated to give the alcohol (367 g) as an amber oil that solidified under high vacuum; NMR: 7.39 (d,1, J=8.2), 7.28 (d,1, J=2.0), 7.04 (dd,1, J=8.2, 2.0), 3.65 (m,1), 3.50 (m,1), 2.90 (m,2), 2.71 (m,1), 2.25 (m,2), 1.86 (m,2).

e. (S)-2-(3,4-Dichlorophenyl)-4-hydroxybutylamine. To a mechanically stirred solution of D-tartaric acid (222 g) in methanol (4 L) at reflux was added the above alcohol (342 g) in warm methanol (2 L) in one portion followed by additional methanol (1 L). The mixture was heated to reflux. Crystals began to form before attaining the boiling point. After 1.5 hours at reflux, the solution was gradually cooled to room temperature and stirred for 3 days. The first crop of tartrate salt was collected by suction filtration and dried in a vacuum oven at 60° C. to give the product (232 g). This material was taken up in methanol (13.5 L) at boiling, and held at reflux for 1 hour allowing 1 L of methanol to distill off. The mixture was allowed to cool gradually to room temperature and stirred for 4 days. The first crop of crystals was collected by suction filtration and dried to give a solid (178.8 g). The methanol filtrate was evaporated to approximately 3 L volume. The resulting suspension was heated back to reflux to give a clear solution that was allowed to cool gradually to room temperature with stirring. A second crop of crystals (43.8 g) was collected. The combined crops of resolved amino alcohol tartrates (222.6 g) were taken up in 1.0 N sodium hydroxide (1.5 L) and extracted with dichloromethane (4 times 500 mL). The combined organic extracts were washed (brine), dried, and evaporated to give the optically enriched alcohol (135.4 g) as an off-white solid; mp 80°–2° C.; MS: m/z=324(M+1); NMR (CD$_3$OD): 7.47 (d,1, J=8.3), 7.42 (d,1, J=2.1), 7.17 (dd,1, J=8.2, 2.1), 3.47 (m,1), 3.34 (m,1), 2.83 (m,3), 1.92 (m,1), 1.74 (m,1).

f. Ethyl (S)-N-[2-(3,4-dichlorophenyl) -4-hydroxybutyl]-carbamate. Ethyl chloroformate (25.5 g) was added dropwise over 20 minutes to a mechanically stirred solution of the above alcohol (50.0 g) and triethylamine (24.9 g) in dichloromethane (600 mL). The internal temperature was maintained at −20° to −25° C. during the addition. The reaction mixture was allowed to warm gradually to room temperature over a 4 hour period, and was washed (1 N hydrochloric acid, saturated aqueous sodium bicarbonate, and saturated aqueous sodium chloride). The separated dichloromethane phase was dried and evaporated to give the carbamate as a yellow oil (65.3 g); MS: m/z=306(M+1); NMR (CD$_3$OD): 7.44 (d,1, J=8.3), 7.38 (d,1, J=2.1), 7.15 (dd,1, J=8.3, 2.1), 3.99 (q,2, J=7.1), 3.45 (m,1), 3.29 (m,3), 2.97 (m,1), 1.92 (m,1), 1.75 (m,1), 1.16 (t,3, J=7.1).

g. (S)-N-[2-(3,4-Dichlorophenyl)-4-hydroxybutyl]methylamine. The above carbamate (65.3 g) in tetrahydrofuran (500 mL) was added dropwise over 30 minutes to a mechanically stirred supension of lithium aluminum hydride (16.0 g) in tetrahydrofuran (200 mL). The internal temperature rose to 45° C. during the addition. The reaction mixture was heated at reflux for 1 hour, cooled to room temperature and stirred overnight. The mixture was cooled in an ice bath, and saturated aqueous sodium sulfate (50 mL) was added dropwise over 45 minutes. After an additional hour of stirring, solid anhydrous sodium sulfate (50 g) was added. After being stirred for 30 minutes, the mixture was filtered through diatomaceous earth, and the filtrate was evaporated to give the amine (52.9 g) as a yellow oil; MS: m/z=248(M+1); NMR: 7.37 (d,1, J=8.2), 7.27 (d,1, J=2.0), 7.01 (dd,1, J=8.2, 2.1), 3.69 (m,1), 3.53 (m,1), 3.40 (m,2), 2.76 (m,3), 2.45 (m,3), 1.89 (m,2).

h. (S)-N-[2-(3,4-Dichlorophenyl)-4-hydroxybutyl]-N-methylbenzamide. Benzoyl chloride (31.5 g) in dichloromethane (200 mL) was added dropwise over 45 minutes to a mechanically stirred solution of the above amine (52.9 g) and triethylamine (54.0 g) in dichloromethane (1 L). An ice bath was Used throughout the addition to maintain an internal temperature of 5°–8° C. The reaction mixture was stirred for 3 hours at room temperature, and washed (1 N hydrochloric acid, brine). The separated dichloromethane layer was evaporated to give a yellow oil which was chromatographed, with dichloromethane:methanol (gradient 100:0, 95:5) as the eluent, to give the benzamide (65.6 g) as a white solid; mp 123°–5° C.; MS: m/z=352(M+1); [α]$_D$=−18.3° (c=2.46, CH$_3$OH).

i. (S)-N-[2-(3,4-Dichlorophenyl)-4-oxobutyl]-N-methylbenzamide. The above benzamide (12.9 g) in dichloromethane (150 mL) was cannulated into a solution of 1,1,1-triacetoxy-1,1-dihydro-1,2-benziodoxol-3-(1H)-one (18.6 g) and tert-butanol (4.5 mL) in dichloromethane (150 mL). After being stirred for 5 minutes, the reaction mixture was diluted with ether (600 mL) and a solution of sodium bicarbonate (19.7 g) and sodium thiosulfate pentahydrate (64.5 g) in water (825 mL). The biphasic system was vigorously stirred until both layers became clear (approximately 30 minutes). The separated organic layer was washed (saturated aqueous sodium bicarbonate), dried, and evaporated. The crude material was chromatographed, with dichloromethane:ether (1:1) as the eluent, to give the aldehyde as a white solid (9.7 g) following precipitation and filtration from ether; MS: m/z=350(M+1).

The intermediate 4-(1-oxoisoindolin-2-yl)piperidine was prepared as follows:

j. 4-tert-Butoxycarbonylaminopiperidine. To a solution of 1-benzyl-4-aminopiperidine (66.2 g) in tetrahydrofuran (275 mL) was added dropwise di-tert-butyl dicarbonate (76.0 g) in tetrahydrofuran (50 mL). After being stirred for 4 hours, the mixture was evaporated and redissolved in 95% ethanol (1250 mL) in a 2 L stainless steel reactor. Palladium on carbon (10%, 13.6 g) in 95% ethanol (100 mL) was added and the mixture was placed under a hydrogen atmosphere (3.44 bar) at 45° C. for 3 hours. The resulting solution was filtered through diatomaceous earth/silica gel and evaporated to give the aminopiperidine (72.5 g) as a white solid; MS: m/z=201(M+1); NMR: 4.61 (m,1), 3.51 (m,1), 3.07 (m,1), 3.03 (m,1), 2.65 (m,2), 1.93 (m,2), 1.58 (m,1), 1.45 (s,9), 1.27 (m,2).

k. 1-Benzyloxycarbonyl-4-tert-butoxycarbonylaminopiperidine. To a solution of N-(benzyloxycarbonyloxy)succinimide (58.5 g) in dichloromethane (300 mL) was added sequentially triethylamine (36.0 mL) and 4-tert-butoxycarbonylaminopiperidine (from Example 1.j.) (47.0 g). After being stirred for 2 hours, the reaction mixture was washed (0.1 N hydrochloric acid, dilute aqueous sodium bicarbonate), and the organic phase was dried and evaporated to give an oil. The addition of ether produced a precipitate that was filtered to give the 1-benzyloxycarbonyl-4-tert-butoxycarbonylaminopiperidine (75 g) as a white solid; NMR: 7.35(m,5), 5.12 (s,2), 4.53 (1,m), 4.10 (m,2), 3.60 (m,1), 2.92 (m,2), 1.92 (m,2), 1.44 (s,9), 1.31 (m,2).

l. 4-Amino-1-benzyloxycarbonylpiperidine. To a solution of the above piperidine (55.0 g) in dichloromethane (300 mL) was added trifluoroacetic acid (90 mL) in 10 mL increments over a period of 20 minutes. After being stirred for 4 hours, the reaction mixture was diluted with water (1 L) and extracted with dichloromethane. The aqueous phase was basified with 1.0 N sodium hydroxide (until pH 10) and extracted with dichloromethane. The combined organic extracts were dried and evaporated to give the amine as an oil that slowly solidified to a white solid (36.5 g); NMR: 7.36 (m,5), 5.12 (s,2), 4.12 (m,2), 2.83 (m,3), 1.80 (m,2), 1.51 (m,2), 1.25 (m,2).

m. 1-Benzyloxycarbonyl-4-phthalimidopiperidine. A solution of 4-amino-1-benzyloxycarbonylpiperidine (5.0 g), N-carbethoxyphthalimide (4.7 g), and triethylamine (4.5 mL) in tetrahydrofuran (100 mL) was allowed reflux for 16 hours. The reaction mixture was evaporated, dissolved in dichloromethane, and washed successively with 0.1 N hydrochloric acid and aqueous sodium bicarbonate. The separated organic layer was dried and evaporated. The crude product was suspended in ether and Filtered to give the title compound (6.7 g) as a white solid; MS: m/z=365(M+1); NMR (CDCl$_3$/CF$_3$COOH): 7.87 (m,2), 7.80 (m,2), 7.38 (m,5), 5.21 (s,2), 4.37 (m,3), 2.97 (m,2), 2.44 (m,2), 1.80 (m,2).

n. 1-Benzyloxycarbonyl-4-(3-hydroxy-1-oxoisoindolin-2-yl)piperidine. Sodium borohydride (4.9 g) was added to a suspension of the imide (4.7 g) in methanol (100 mL) at 0° C. After being stirred for 1.25 hours, the reaction mixture was diluted with aqueous sodium bicarbonate and extracted with dichloromethane. The organic extracts were dried and evaporated to give the title compound, which was contaminated with an undetermined amount of 1-benzyloxycarbonyl-4-(2-hydroxymethylbenzamido)piperidine, as a foamy white solid (4.5 g); MS: m/z=349 [(M+1)—OH]; NMR (CD$_3$OD): 7.70 (m,1), 7.61 (m,2), 7.53 (m,1), 7.36 (m,5), 5.97 (s,1), 5.14 (s,2), 4.30 (m,2), 4.13 (m,1), 2.95 (m,2), 2.19 (m,1), 2.07 (m,1), 1.89 (m,2).

o. 1-Benzyloxycarbonyl-4-(1-oxoisoindolin-2-yl)piperidine. Trifluoroacetic acid (12.5 mL) was added dropwise to a solution of the aminal (2.9 g) and triethylsilane (12.9 mL) in chloroform. After being stirred overnight, the reaction mixture was neutralized with saturated aqueous sodium bicarbonate, diluted with water, and extracted with dichloromethane. The organic extracts were dried, diluted with toluene (to remove excess triethylsilane during evaporation), and evaporated. The material was suspended in ether and filtered. The solid (1.0 g) was chromatographed, with dichloromethane:ether (gradient 100:0, 0:100) as the eluent, to give 1-benzyloxycarbonyl-4-(1-oxoisoindolin-2-yl)piperidine (380 mg) as a white solid; MS: m/z=351(M+1); NMR (CDCl$_3$/CF$_3$COOH): 7.87 (m,1), 7.67 (m,1), 7.56 (m,2), 7.38 (m,5), 5.20 (s,2), 4.53 (m,1), 4.49 (bs,2), 4.37 (m,2), 3.05 (m,2), 1.97 (m,2), 1.77 (m,2).

p. 4-(1-Oxoisoindolin-2-yl)piperidine. A solution of the 1-benzyloxycarbonyl-4-(1-oxoisoindolin-2-yl)piperidine (350 mg) and 20% palladium hydroxide on carbon (100 mg) in ethanol (6 mL) and tetrahydrofuran (2 mL) was stirred overnight under hydrogen (1 bar). The reaction mixture was filtered through diatomaceous earth, and the filtrate was evaporated to give 4-(1-oxoisoindolin-2-yl)piperidine (200 mg) as a white solid; MS: m/z=217(M+1); NMR (CD$_3$OD): 7.76 (m,1), 7.58 (m,2), 7.49 (m,1), 4.50 (s,2), 4.27 (m,1), 3.15 (m,2), 2.74 (m,2), 1.82 (m,4).

EXAMPLE 2

(S)-N-[2-(3,4-Dichlorophenyl)-4-[4-(2-oxo-2,3-dihydro-benzimidazol-1-yl)piperidino]butyl]-N-methylbenzamide hydrochloride Using a procedure similar to that described in Example 1, except replacing 4-(1-oxoisoindolin-2-yl)piperidine with 4-(2-oxo-2,3-dihydrobenzimidazol-1-yl)piperidine, the title compound was obtained as a white solid; MS: m/z=551(M+1). Analysis for C$_{30}$H$_{32}$Cl$_2$N$_4$O$_2$·1.50 HCl·0.30 (CH$_3$CH$_2$)$_2$O: Calculated: C, 59.63; H, 5.85; N, 8.91; Found: C, 59.65; H, 5.84; N, 8.97.

EXAMPLE 3

(S)-N-[2-(3,4-Dichlorophenyl)-4-[4-(2-oxo-1,2,3,4-tetrahydroquinazolin-3-yl)piperidino]butyl]-N-methylbenzamide citric acid salt (1:1)

Using a procedure similar to that described in Example 1, except replacing 4-(1-oxoisoindolin-2-yl)piperidine with 4-(2-oxo-1,2,3,4-tetrahydroquinazolin-3-yl)piperidine and dissolving the chromatographed product in methanol containing abut 1 equivalent of citric acid and evaporating, the title salt was prepared. The resulting glass was pulverized as a suspension in ether and the solvent was evaporated to give the title compound as a white solid; MS: m/z=565(M+1). Analysis for C$_{31}$H$_{34}$Cl$_2$N$_4$O$_2$·1.05 C$_6$H$_8$O$_7$·0.6 H$_2$O: Calculated: C, 57.57; H, 5.64; N, 7.20; Found: C, 57.56; H, 5.73; N, 7.14.

The intermediate 4-(2-oxo-1,2,3,4-tetrahydroquinazolin-3-yl)piperidine was prepared as follows:

a. 8-Benzyloxycarbonyl-1,4-dioxa-8-azaspiro[4.5]decane. To a solution of 1,4-dioxa-8-azaspiro[4.5]decane (45.9 g) in dichloro-methane (600 mL) was added N-(benzyloxycarbonyloxy)succinimide (81.5 g) in portions. After being stirred for 2 hours, the mixture was quenched with saturated aqueous sodium bicarbonate and stirred overnight as a biphasic mixture. The mixture was diluted with water (1 L), and the dichloromethane layer was dried and evaporated to give 8-benzyloxycarbonyl-1,4-dioxa-8-azaspiro[4.5]decane (86.0 g) as a colorless oil; MS: m/z=278(M+1); NMR: 7.35 (m,5), 5.13 (s,2), 3.96 (s,4), 3.59 (m,4), 1.67 (m,4).

b. 1-Benzyloxycarbonyl-4-piperidone. To a solution of 8-benzyloxycarbonyl-1,4-dioxa-8-azaspiro[4.5]decane (85 g) in tetrahydrofuran (500 mL) was added concentrated hydrochloric acid (100 mL) in water (200 mL), and the resulting solution was allowed to stir for 4 days. The mixture was diluted with water and extracted with dichloromethane. The organic extracts were washed (saturated aqueous sodium bicarbonate), dried, and evaporated to give the ketone (68.0 g) as an oil; MS: m/z=234(M+1); NMR: 7.37 (m,5), 5.18 (s,2), 3.80 (m,4), 2.46 (m,4).

c. 4-(2-Aminobenzylamino)-1-benzyloxycarbonylpiperidine. 1-Benzyloxycarbonyl-4-oxopiperidine (18.3 g) in methanol (80 mL) was added dropwise to a solution of 2-aminobenzylamine (8.0 g) and acetic acid (3.8 mL) in methanol (80 mL). After 30 minutes, sodium cyanoborohydride (4.1 g) in methanol (80 mL) was added dropwise. After being stirred overnight, the reaction mixture was quenched with saturated aqueous sodium bicarbonate, concentrated in vacuo, dissolved in dichloromethane, and Washed with water. The separated organic layer was dried and evaporated. The crude viscous oil was dissolved in ether which resulted in the formation of a precipitate. The solids were collected by filtration to give the title compound (15 g) as a white powder; MS: m/z=340(M+1); NMR (CD$_3$OD): 7.34 (m,5), 7.03 (m,2), 6.70 (m,2), 5.10 (s,2), 4.07 (m,2), 3.78 (s,2), 2.91 (m,2), 2.69 (m,1), 1.93 (m,2), 1.29 (m,2).

d. 1-Benzyloxycarbonyl -4-(2-oxo-1,2,3,4-tetrahydroquinazolin-3-yl) piperidine. A stirred solution of 4-(2-aminobenzylamino)-1-benzyloxycarbonylpiperidine (3.2 g), 4-dimethylaminopyridine (1.2 g), and [bis(trichloromethyl)carbonate] (940 mg) in chloroform (70 mL) was refluxed for 30 minutes. The reaction mixture was diluted with dichloromethane and washed successively with 1.0 N hydrochloric acid and aqueous sodium bicarbonate. The separated organic layer was dried and evaporated. The crude product was chromatographed, with dichloromethane:ether:methanol (gradient 50:50:0, 20:80:0, 80:0:20)as the eluent, to give 1-benzyloxycarbonyl-4-(2-oxo-1,2,3,4-tetrahydro-quinazolin-3-yl) piperidine as a white solid (2.5 g); MS: m/z=366(M+1); NMR: 7.62 (m,1), 7.37 (m,4), 7.17 (m,1), 7.04 (m,1), 6.94 (m,1), 6.71 (m,1), 5.15 (broad s,2), 4.58 (m,1), 4.33 (m,2), 4.30 (s,2), 2.92 (m,2), 1.73 (m,4).

e. 4-(2-Oxo-1,2,3,4-tetrahydroquinazolin-3-yl)piperidine. A solution of 1-benzyloxycarbonyl-4-(2-oxo-1,2,3,4-tetrahydroquinazolin-3-yl)-piperidine (1.9 g) and 20% palladium hydroxide on carbon (400 mg) in ethanol (50 mL) and dichloromethane (50 mL) was stirred for 2.5 hours under hydrogen (1 bar). The reaction mixture was filtered through diatomaceous earth, and the filtrate was evaporated. The crude product was chromatographed, with dichloromethane:methanol (gradient 90:10, 70:10) as the eluent, to give 4-(2-oxo-1,2,3,4-tetrahydroquinazolin-3-yl) piperidine (750 mg) as a white solid; MS: m/z=232(M+1); NMR (CD$_3$OD): 7.14 (m,2), 6.94 (m,1), 6.79 (m,1), 4.42 (s,2), 4.40 (m,1), 3.39 (m,2), 2.99 (m,2), 2.06 (m,2), 1.85 (m,2).

Formulae

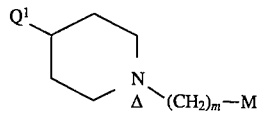

I

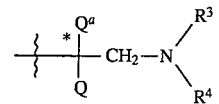

Ia

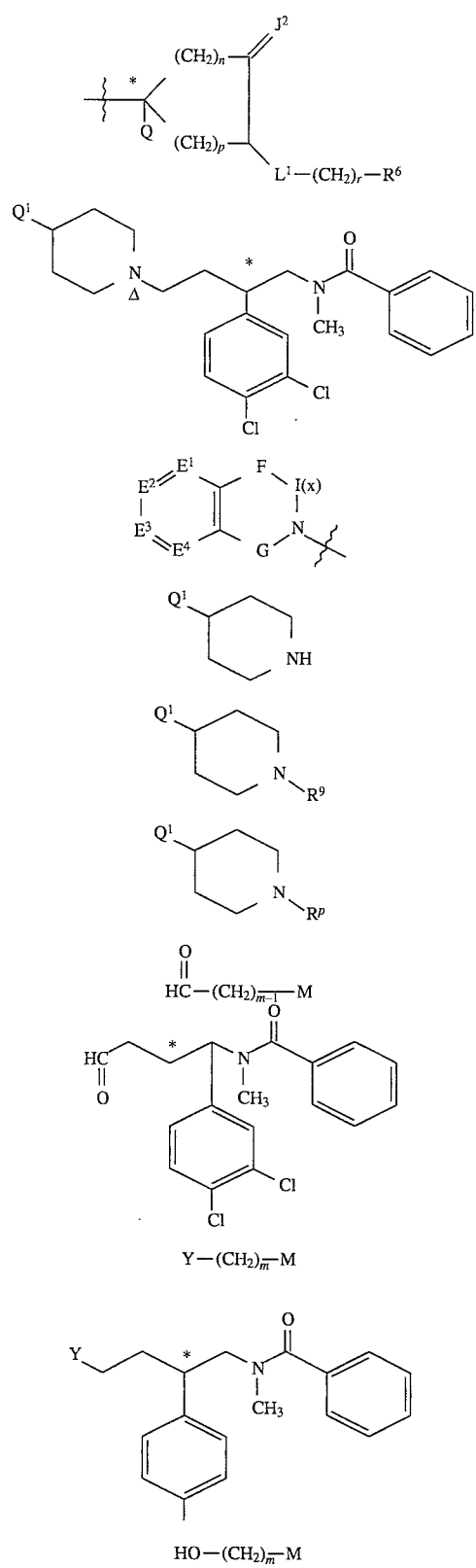
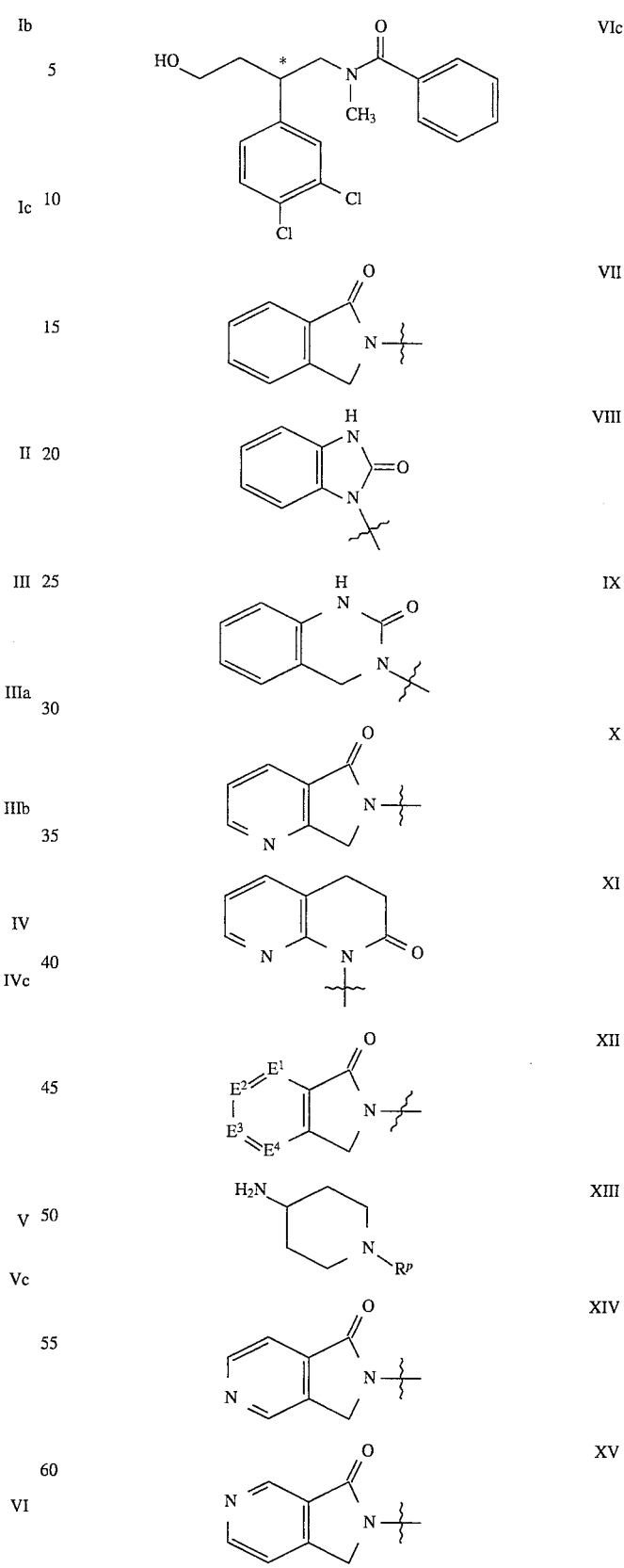

-continued
Formulae

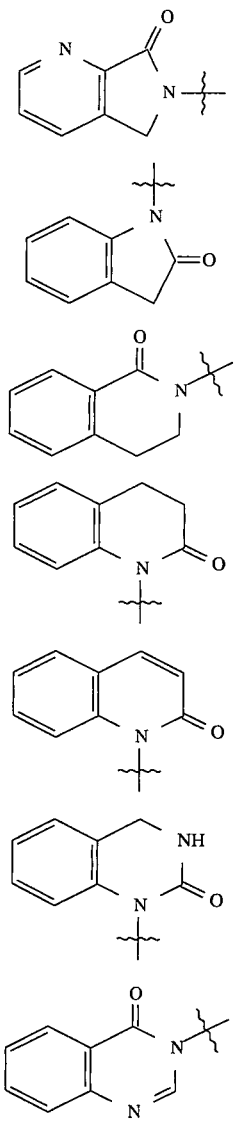

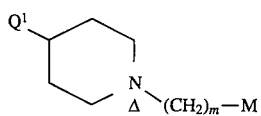

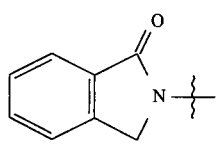

What is claimed is:

1. A compound of formula I:

$$Q^1 \text{—piperidine—} N\text{—(CH}_2)_m\text{—M} \quad (I)$$

(with Δ notation)

wherein:

$Q_1$ is a nitrogen linked radical selected from the radicals of formulae VII–IX:

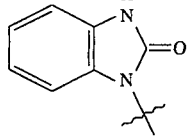 (VII)

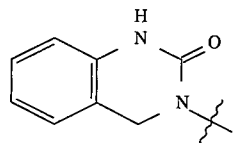 (VIII)

(IX) [structure shown]

m is 2 or 3;

M is a residue of formula Ia or formula Ib:

$$\text{(Ia)} \quad *\!-\!\overset{Q^a}{\underset{Q}{C}}\!-\!CH_2\!-\!N\!\begin{smallmatrix}R^3\\R^4\end{smallmatrix}$$

$$\text{(Ib)} \quad *\!-\!\overset{(CH_2)_n}{\underset{(CH_2)_p}{C}}\!\begin{smallmatrix}J^2\\ \\L^1\!-\!(CH_2)_r\!-\!R^6\end{smallmatrix}$$

wherein Q is phenyl which may bear one or two substituents independently selected from halo, trifluoromethyl, hydroxy, (1–3C)alkoxy, (1–3C)alkyl land methylenedioxy; or Q is thienyl, imidazolyl, benzo thiophenyl or naphthyl any of which may bear a halo substituent; or Q is biphenylyl; or Q is carbon-linked indolyl which may bear a benzyl substituent at the 1-position;

$Q^a$ is hydrogen, (1–4C)alkyl, or a radical of formula —(CH$_2$)$_q$—NR$^7$R$^8$ in which q is 2 or 3 and R$^7$ and R$^8$ are independently (1–4C)alkyl or NR$^7$R$^8$ is piperidino or 4-benzylpiperidino;

$R^3$ is hydrogen, methyl or (2–6C)n-alkyl which may bear a terminal amino radical;

$R^4$ is —C(=O)R$^5$, —C(=O)OR$^5$ or —C(=J$^1$)NHR$^5$ in which J$^1$ is oxygen or sulfur and R$^5$ is hydrogen, (1–6C)alkyl, phenyl(1–3C)alkyl (in which the phenyl may bear one or more halo, hydroxy, (1–4C)alkoxy or (1–4C)alkyl substituents), pyridyl(1–3C)alkyl, naphthyl(1–3C)alkyl, pyridylthio(1–3C)alkyl, styryl, 1-methylimidazol-2-ylthio(1–3C)alkyl, aryl (which may bear one or more halo, hydroxy, (1–4C)alkoxy or (1–4C)alkyl substituents), heteroaryl (which may bear one or more halo, hydroxy, (1–4C)alkoxy or (1–4C)alkyl substituents), or (when R$^4$ is —COR$^5$) α-hydroxybenzyl;

n is 0, 1, 2 or 3;

p is 1 or 2, and when p is 2, n is 1 and J$^2$ is two hydrogens;

J$^2$ is oxygen or two hydrogens;

L$^1$ is carbonyl or methylene;

r is 0, 1, 2, or 3; and

R$^6$ is phenyl which may bear one or more halo, trifluoromethyl, (1–4C)alkyl, hydroxy or (1–4C)alkoxy substituents (and particularly one or more chloro or fluoro substituents); naphthyl which may bear one or more halo, trifluoromethyl, (1–4C)alkyl or hydroxy substituents; pyridyl; thienyl; indolyl; quinolinyl; benzothienyl or imidazolyl; or when L¹ is carbonyl, the group —(CH₂)ᵣ—R₆ may be a benzyl group bearing an α-substituent selected from hydroxy, (1–4C)alkoxy and (1–4)alkyl, and further wherein the phenyl portion of the benzyl group may bear one or more substituents selected independently from halo, trifluoromethyl, (1–4C)alkyl, hydroxy (1–4C)alkyl, hydroxy and (1–4C)alkoxy; or the N-oxide of the piperidino nitrogen indicated by Δ; or a pharmaceutically acceptable salt thereof; or a quaternary ammonium salt thereof in which the piperidino nitrogen indicated by Δ is a quadricovalent ammonium nitrogen wherein the fourth radical on the nitrogen R⁹ is (1–4C)alkyl or benzyl and the associated counterion A is a pharmaceutically acceptable anion.

2. A compound as claimed in claim 1 wherein said compound of formula I is a compound of formula Ic:

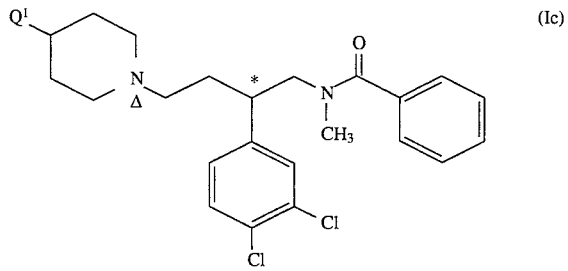

or the N-oxide of the piperidino nitrogen indicated by Δ; or a pharmaceutically acceptable salt thereof; or a quaternary ammonium salt thereof in which the piperidino nitrogen indicated by Δ is a quadricovalent ammonium nitrogen wherein the fourth radical on the nitrogen R⁹ is (1–4C)alkyl or benzyl and the associated counterion A is a pharmaceutically acceptable anion.

3. A compound as claimed in claim 1, wherein M is formula Ib; and n is 1 or 2; p is 1; J₂ is two hydrogens; L¹ is carbonyl; r is 0 or 1; and R⁶ is phenyl which may bear one or two halo or (1–4C)alkoxy substituents; or the N-oxide of the piperidino nitrogen indicated by Δ; or a pharmaceutically acceptable salt thereof; or a quaternary ammonium salt thereof in which the piperidino nitrogen indicated by Δ is a quadricovalent ammonium nitrogen wherein the fourth radical on the nitrogen R⁹ is (1–4C)alkyl or benzyl and the associated counterion A is a pharmaceutically acceptable anion.

4. A compound as claimed in claim 1 or 3, wherein m is 2; or the N-oxide of the piperidino nitrogen indicated by Δ; or a pharmaceutically acceptable salt thereof; or a quaternary ammonium salt thereof in which the piperidino nitrogen indicated by Δ is a quadricovalent ammonium nitrogen wherein the fourth radical on the nitrogen R⁹ is (1–4C)alkyl or benzyl and the associated counterion A is a pharmaceutically acceptable anion.

5. A compound as claimed in claim 1 which is selected from: (S)-N-[2-(3,4-dichlorophenyl)-4-[4-(1-oxoisoindolin-2-yl) piperidino]butyl]-N-methylbenzamide; (S)-N-[2-(3,4-dichlorophenyl)-4-[4-(2-oxo-2,3-dihydrobenzimida-1-yl)piperidino]butyl]-N-methylbenzamide; and (S)-N-[2-(3,4-dichlorophenyl)-4-[4-(2-oxo1,2,3,4-tetrahydroquinazolin-3-yl) piperidino]butyl]-N-methylbenzamide; or the N-oxide of the piperidino nitrogen indicated by Δ; or a pharmaceutically acceptable salt thereof; or a quaternary ammonium salt thereof in which the piperidino nitrogen indicated by Δ is a quadricovalent ammonium nitrogen wherein the fourth radical on the nitrogen R⁹ is (1–4C)alkyl or benzyl and the associated counterion A is a pharmaceutically acceptable anion.

6. A pharmaceutical composition comprising an effective amount of a compound of formula I; or the N-oxide of the piperidino nitrogen indicated by Δ; or a pharmaceutically acceptable salt thereof; or a quaternary ammonium salt thereof in which the piperidino nitrogen indicated by Δ is a quadricovalent ammonium nitrogen wherein the fourth radical on the nitrogen R⁹ is (1–4C)alkyl or benzyl and the associated counterion A is a pharmaceutically acceptable anion; as defined in claim 1; and a pharmaceutically acceptable diluent or carrier.

7. A method of treating a disease in a human or other mammal in need thereof in which E is implicated and antagonism of its action is desired, comprising: administering an effective amount of a compound of formula I; or the N-oxide of the piperidino nitrogen indicated by Δ; or a pharmaceutically acceptable salt thereof; or a quaternary ammonium salt thereof in which the piperidino nitrogen indicated by Δ is a quadricovalent ammonium nitrogen wherein the fourth radical on the nitrogen R⁹ is (1–4C)alkyl or benzyl and the associated counterion A is a pharmaceutically acceptable anion; as described in claim 1.

8. A method treating a disease as described in claim 7 wherein the disease is asthma.

* * * * *

UNITED STATES PATENT AND TRADEMARK OFFICE
CERTIFICATE OF CORRECTION

PATENT NO.    :   5,602,138

DATED         :   February 11, 1997

INVENTOR(S)   :   Scott Carson Miller

It is certified that error appears in the above-identified patent and that said Letters Patent is hereby corrected as shown below:

Column 17, line 45,

"
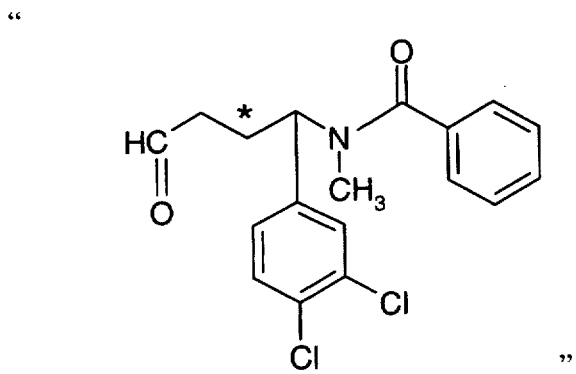
"

should read

--
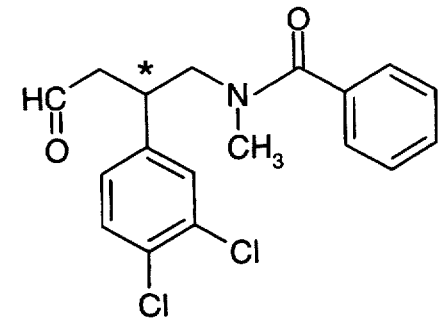
--.

Column 20, line 31, "land" should read --and--.

UNITED STATES PATENT AND TRADEMARK OFFICE
CERTIFICATE OF CORRECTION

PATENT NO.      :   5,602,138

DATED           :   February 11, 1997

INVENTOR(S)     :   Scott Carson Miller

It is certified that error appears in the above-identified patent and that said Letters Patent is hereby corrected as shown below:

Column 22, line 12, "(2-oxo-2,3-dihydrobenzimida-1-yl)" should read --(2-oxo-2,3-dihydrobenzimidazol-1-yl)--.

Column 22, line 14, "[4-(2-oxo1,2,3,4-tetrahydroquinazolin-3-" should read --[4-(2-oxo-1,2,3,4-tetrahydroquinazolin-3---.

Column 22, line 34, "in which E is implicated and" should read --in which NKA is implicated and--.

Signed and Sealed this

Twenty-fifth Day of August, 1998

Attest:

BRUCE LEHMAN

*Attesting Officer*          *Commissioner of Patents and Trademarks*